United States Patent
Sillman et al.

(10) Patent No.: US 8,285,517 B2
(45) Date of Patent: Oct. 9, 2012

(54) METHOD FOR TRACKING AND REPORTING USAGE EVENTS TO DETERMINE WHEN PREVENTIVE MAINTENANCE IS DUE FOR A MEDICAL ROBOTIC SYSTEM

(75) Inventors: Debra Sillman, Los Altos, CA (US); Gregory K. Toth, Los Altos, CA (US); Thomas Nixon, Santa Clara, CA (US); Robert P Sundstrom, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 12/916,059

(22) Filed: Oct. 29, 2010

(65) Prior Publication Data

US 2011/0098861 A1 Apr. 28, 2011

Related U.S. Application Data

(62) Division of application No. 11/556,731, filed on Nov. 6, 2006, now Pat. No. 7,835,823.

(60) Provisional application No. 60/756,441, filed on Jan. 5, 2006.

(51) Int. Cl.
*G06F 17/40* (2006.01)
*B25J 9/22* (2006.01)

(52) U.S. Cl. ............ 702/187; 606/130; 700/27; 700/79; 700/175; 700/254; 702/34; 702/184; 323/911

(58) Field of Classification Search ............... 702/59
See application file for complete search history.

(56) References Cited

U.S. PATENT DOCUMENTS

| | | | |
|---|---|---|---|
| 4,512,442 A | | 4/1985 | Moore et al. |
| 5,210,704 A | * | 5/1993 | Husseiny .................... 702/34 |
| 5,400,267 A | * | 3/1995 | Denen et al. ................. 702/59 |
| 6,151,039 A | * | 11/2000 | Hmelar et al. ................. 347/7 |
| 6,246,200 B1 | | 6/2001 | Blumenkranz et al. |
| 6,331,181 B1 | * | 12/2001 | Tierney et al. ............ 606/130 |
| 6,370,411 B1 | | 4/2002 | Osadchy et al. |
| 6,584,430 B1 | * | 6/2003 | Rosenbaum et al. ....... 702/183 |

(Continued)

OTHER PUBLICATIONS

PCT/US06/62026 International Search Report and Written Opinion of the International Searching Authority, mailed Apr. 28, 2008, 13 pages.

(Continued)

*Primary Examiner* — Thomas Black
*Assistant Examiner* — Lin B Olsen

(57) ABSTRACT

A medical robotic system comprises a number of components that may be monitored to determine their preventive maintenance needs by recording usage-related information for the monitored components into associated non-volatile memories. When usage of the component exceeds a specified usage threshold, the system displays a warning message on its display screen to have preventive maintenance performed for the component. If the usage continues without such maintenance and exceeds a higher usage threshold, the system displays an error message on its display screen and the system transitions into an error state during which medical procedures are not allowed to be performed. The usage-related information may also be communicated to a remote computer which gathers and processes usage-related information from a number of medical robotic systems to estimate resource requirements for timely performing preventive maintenance on the medical robotic systems, and anticipated service revenues from such maintenance.

35 Claims, 12 Drawing Sheets

U.S. PATENT DOCUMENTS

| | | | |
|---|---|---|---|
| 6,611,793 B1 * | 8/2003 | Burnside et al. | 702/183 |
| 6,922,597 B2 * | 7/2005 | Mailliet et al. | 700/79 |
| 7,048,745 B2 | 5/2006 | Tierney et al. | |
| 7,357,774 B2 | 4/2008 | Cooper | |
| 7,400,983 B2 * | 7/2008 | Feingold et al. | 702/31 |
| 7,524,320 B2 | 4/2009 | Tierney et al. | |
| 2002/0032380 A1 | 3/2002 | Acker et al. | |
| 2002/0193969 A1 * | 12/2002 | Frantz et al. | 702/188 |
| 2003/0009154 A1 | 1/2003 | Whitman | |
| 2003/0171836 A1 * | 9/2003 | Yajima et al. | 700/108 |
| 2003/0208196 A1 | 11/2003 | Stone | |
| 2005/0273642 A1 | 12/2005 | Moore | |
| 2006/0095096 A1 * | 5/2006 | DeBenedictis et al. | 607/88 |
| 2006/0129269 A1 * | 6/2006 | Conner et al. | 700/175 |
| 2007/0024845 A1 | 2/2007 | Essling et al. | |
| 2007/0083286 A1 | 4/2007 | Kobayashi | |

OTHER PUBLICATIONS

Vertut, Jean and Phillipe Coiffet, *Robot Technology: Teleoperation and Robotics Evolution and Development*, English translation Prentice-Hall, Inc., Inglewood Cliffs, NJ, USA 1986, vol. 3A, 332 pages.

* cited by examiner

METHOD FOR TRACKING AND REPORTING USAGE EVENTS TO DETERMINE WHEN PREVENTIVE MAINTENANCE IS DUE FOR A MEDICAL ROBOTIC SYSTEM

CROSS REFERENCE TO RELATED APPLICATIONS

This application is a divisional of U.S. application Ser. No. 11/556,731 filed Nov. 6, 2006 which claims priority to U.S. provisional application Ser. No. 60/756,441 filed Jan. 5, 2006, each of which is incorporated herein by reference.

FIELD OF THE INVENTION

The present invention generally relates to medical robotic systems and in particular, to a method for tracking and reporting usage events to determine when preventive maintenance is due for a medical robotic system.

BACKGROUND OF THE INVENTION

Medical robotic systems such as those used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for minimally invasive surgery using medical robotic systems is strong and growing.

One example of a medical robotic system is the daVinci® Surgical System from Intuitive Surgical, Inc., of Sunnyvale, Calif. The daVinci® system includes a surgeon's console, a patient-side cart, a high performance 3-D vision system, and Intuitive Surgical's proprietary EndoWrist™ articulating instruments, which are modeled after the human wrist so that when added to the motions of the robotic arm assembly holding the surgical instrument, they allow at least six degrees of freedom of motion, which is comparable to the natural motions of open surgery.

The daVinci® surgeon's console has a high-resolution stereoscopic video display with two progressive scan cathode ray tubes ("CRTs"). The system offers higher fidelity than polarization, shutter eyeglass, or other techniques. Each eye views a separate CRT presenting the left or right eye perspective, through an objective lens and a series of mirrors. The surgeon sits comfortably and looks into this display throughout surgery, making it an ideal place for the surgeon to display and manipulate 3-D intraoperative imagery.

During a surgical procedure, it is generally desirable that the medical robotic system be reliable with an unlikelihood of system failure. Thus, it is desirable to timely perform preventive maintenance before any system failure. In addition, it would be useful to be able to predict when preventive maintenance will be required for field installed systems in order to plan service resource needs as well as service revenues for system manufacturers.

Commonly owned U.S. Pat. No. 7,048,745, the full disclosure of which is incorporated herein by this reference, describes storing tool life data (such as the number of times the tool has been loaded onto a surgical system, the number of surgical procedures performed with the tool, and/or the total time the tool has been used) in a non-volatile memory, wherein an expired tool may provide an indication to the system operator such as a pop-up flag, a color-change spot, or the like, to indicate that the tool is at or near the end of its life.

Although providing a visual end-of-use indication on the tool itself is useful to notify a locally situated assistant or surgeon that a surgical tool should be replaced, it may not serve to readily inform a surgeon who is seated at a surgeon's console some distance away from the tool of such need. Also, in addition to surgical tools which are relatively easy to replace even during a medical procedure, there are many other components of a medical robotic system that require periodic maintenance or replacement, but are not readily removed and replaced during a medical procedure. It would therefore be useful to monitor such components for preventive maintenance needs, and inform the surgeon of any desirable or necessary preventive maintenance before commencement of a medical procedure for patient safety reasons. It would also be useful if monitored usage data is stored and made available for service resource and revenue planning purposes.

OBJECTS AND SUMMARY OF THE INVENTION

Accordingly, an object of aspects of the present invention is a preventive maintenance method for a medical robotic system that determines preventive maintenance needs on a subsystem basis.

Another object of aspects of the present invention is a preventive maintenance method for a medical robotic system that stores subsystem usage-related information so as to travel with the subsystem.

Another object of aspects of the present invention is a preventive maintenance method for a medical robotic system that provides warnings and/or error messages of preventive maintenance needs to a user of the medical robotic system.

Another object of aspects of the present invention is a preventive maintenance method for a medical robotic system that stores subsystem usage-related information so as not to be lost when power to the system is turned off.

Another object of aspects of the present invention is a method for centrally estimating future preventive maintenance needs for a number of medical robotic systems.

These and additional objects are accomplished by the various aspects of the present invention, wherein briefly stated, one aspect is preventive maintenance method for a medical robotic system, comprising: storing usage-related information for components of the medical robotic system in non-volatile memories respectively associated with the components; determining whether one or more usage thresholds for the components are exceeded according to the stored usage-related information; and displaying messages on a display screen of the medical robotic system identifying individual of the components recommended for preventive maintenance based upon such determination of whether one or more usage thresholds for the components are exceeded.

Another aspect is an improvement to a medical robotic system including a patient-side unit having robotic arms adapted to hold and manipulate medical devices, and a surgeon console having a display screen and a processor configured to control movement of the robotic arms and manipulation of the medical devices. The patient-side unit and surgeon console each include a plurality of subassemblies. The improvement comprises: individual of the plurality of subassemblies configured to store its usage-related information in a non-volatile memory included in the subassembly; and the processor further configured to determine whether one or more usage thresholds have been exceeded according to the usage-related information, and display one or more messages on the display screen identifying individual of the subassemblies requiring preventive maintenance according to such determination.

Another aspect is a method for monitoring preventive maintenance needs for a plurality of medical robotic systems, comprising: periodically receiving usage information for monitored components from each of the plurality of medical robotic systems; and processing the periodically received usage information to estimate when preventive maintenance will be required for each of the monitored components of the plurality of medical robotic systems.

Additional objects, features and advantages of the various aspects of the present invention will become apparent from the following description of its preferred embodiment, which description should be taken in conjunction with the accompanying drawings.

DETAILED DESCRIPTION OF THE PREFERRED EMBODIMENT

Medical robotic systems used for surgery, diagnosis and other medical procedures generally involve the use of multiple robotic arms for holding and manipulating various medical devices. For example, one or more of the robotic arms may support a surgical tool which may be articulated (such as jaws, scissors, graspers, needle holders, micro dissectors, staple appliers, tackers, suction/irrigation tools, clip appliers, or the like) or non-articulated (such as cutting blades, cautery probes, irrigators, catheters, suction orifices, or the like). Another one or more of the arms may be used to support an image capture device such as an endoscope (which may be any of a variety of structures such as a laparoscope, an arthroscope, a hysteroscope, or the like), or, optionally, some other imaging modality (such as ultrasound, fluoroscopy, magnetic resonance imaging, or the like). Typically, the arms will support at least two surgical tools corresponding to the two hands of a surgeon and one image capture device.

Mounting the robotic arms to a single cart structure allows the medical robotic system to be moved efficiently from operating room to operating room. This can avoid construction of specialized robotic operating rooms, and can allow a hospital to take advantage of the flexibility of robotic surgery to perform a variety of surgical procedures, including open surgery, neurosurgical procedures (such as stereotaxy), endoscopic procedures (such as laparoscopy, arthroscopy, thoracoscopy), and the like. However, the scope of the present invention is not be limited to such carts, and is to be understood to include other patient-side units such as those releaseably attaching to the ceiling or operating table.

Mounting of multiple robotic arms on a common base (such as the base of the patient-side cart) allows the computer system that controls robotic movements to determine the position of the end effectors (of the medical devices) and robotic arms relative to each other. This can be used for a variety of purposes, including transforming an image capture coordinate system to a hand input controller coordinate system so as to align the surgeon's inputs with movements of the end effectors as displayed to the surgeon. In some embodiments, the computer may also calculate the positions of the robotic arms relative to each other so as to avoid interference as the medical devices are manipulated during surgery or other medical procedure. For example, solid modeling of the robotic arm structures may be used to prevent two arms from striking each other, thereby avoiding damage to the robotic structure and potential injury to the patient. This common base may also maximize access to the patient before, during, and after the robotic surgical procedure, as the cart (or other patient-side unit) will typically be situated along one side of the operating table, leaving the other side available for access by surgeons and surgical assistants.

Figure 1:
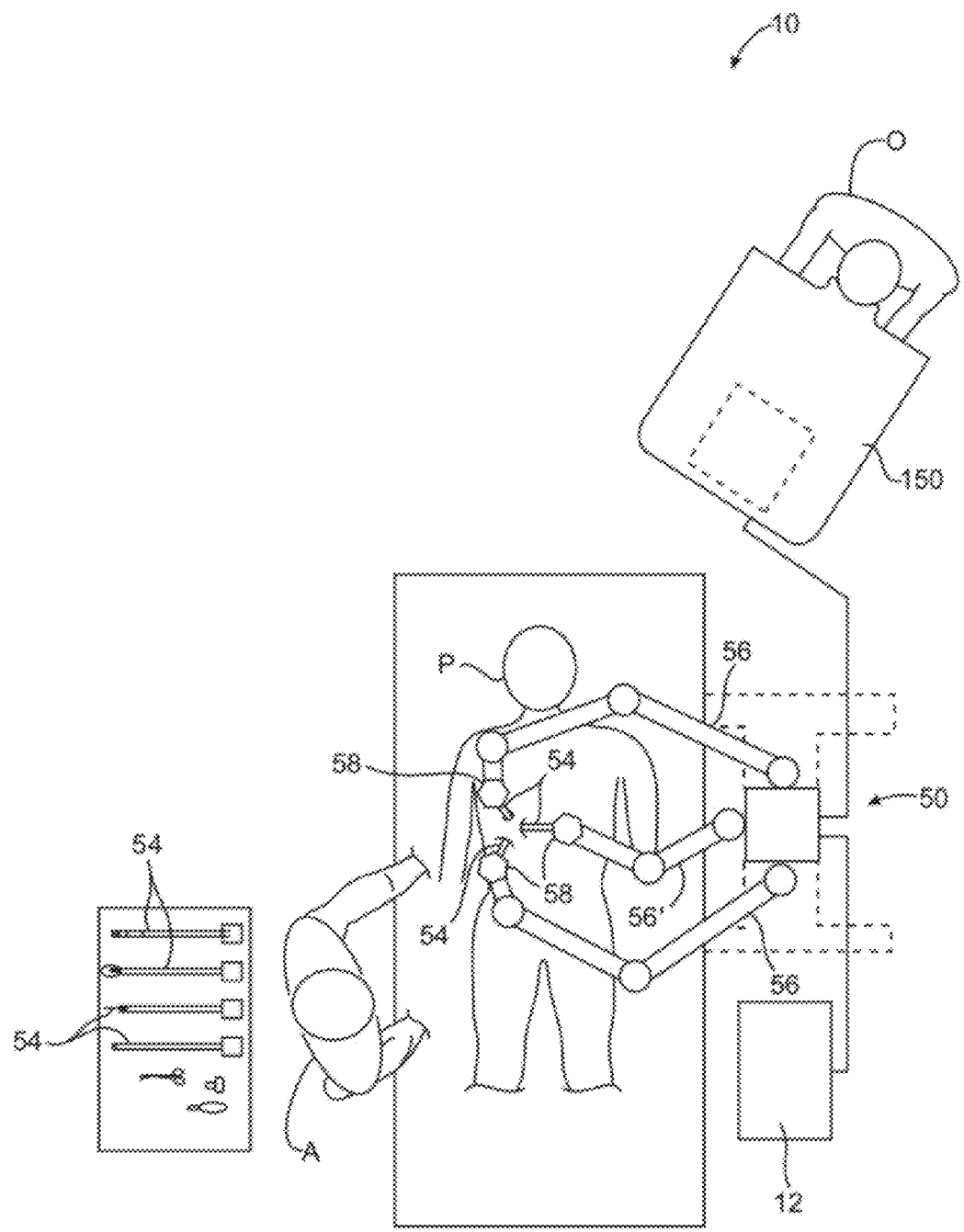
FIG. 1 illustrates a top view of an operating room employing a medical robotic system utilizing aspects of the present invention.

FIG. 1 illustrates, as an example, a top view of an operating room employing a medical robotic system of the present invention. An Operator O (generally a Surgeon) performs a minimally invasive surgical procedure on Patient P by manipulating input devices at a Surgeon Console 150. One or more processors of the Console 150 directs movement of endoscopic surgical instruments 54, effecting movement of the instruments using a patient-side cart 50. An Assistant A assists in pre-positioning of the robotic arms relative to Patient P, and swapping tools or instruments 54 for alternative tool structures, and the like, while viewing the internal surgical site via an assistant display 12. The image of the internal surgical site shown to Assistant A and Operator O respectively on the assistant display 12 and Surgeon Console 150 is provided by an image capturing device, such as an endoscope, supported by cart 50. Typically, the patient-side cart 50 includes at least three robotic arms with a central arm supporting an endoscope and the outer arms supporting tissue manipulation tools.

Generally, the robotic arms of the patient-side cart 50 will include a positioning portion 56 which remains in a fixed configuration while manipulating tissue, and a driven portion 58 which is actively articulated under the direction of Surgeon at the Surgeon Console 150. The actively driven portion is herein referred to as a slave manipulator 58. The fixable portion of the cart linkage structures may be referred to as a positioning linkage 56, 56'.

Figure 2:
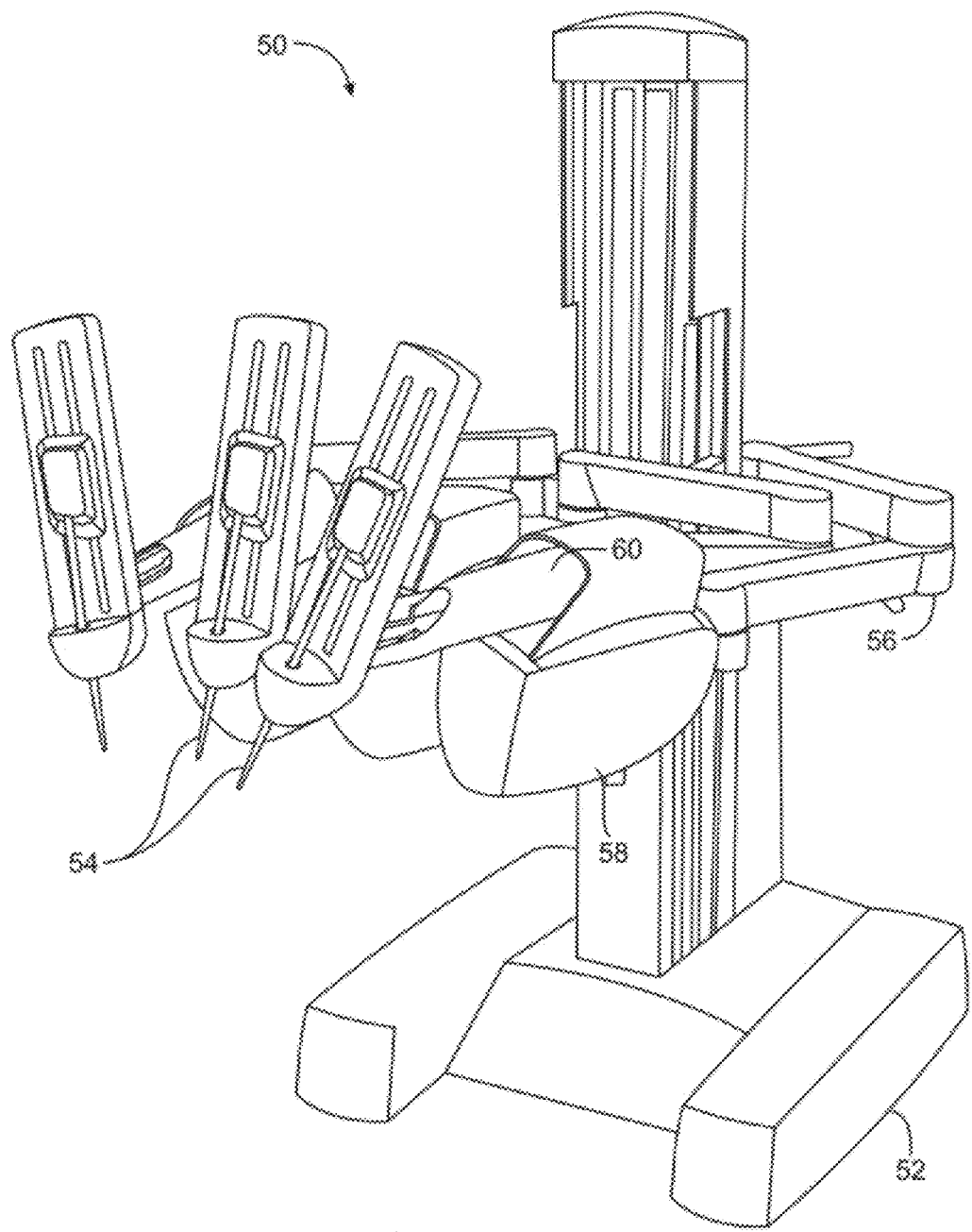
FIG. 2 illustrates a perspective view of a patient-side cart included in a medical robotic system, utilizing various aspects of the present invention.

FIG. 2 illustrates, as an example, a perspective view of the patient-side cart 50. The cart 50 includes a base 52 from which three medical devices (which in this example, are surgical instruments or tools) 54 are supported. More specifically, the medical devices 54 are each supported by a robotic arm including a positioning linkage 56 and a slave manipulator 58. It should be noted that these structures are illustrated in this figure with protective covers extending over much of the robotic arms. It should be understood, however, that these protective covers are optional, and may be limited in size or entirely eliminated in some embodiments to minimize the inertia that is manipulated by the servomechanism, and to limit the overall weight of the patient-side cart 50.

Cart 50 will generally have dimensions suitable for transporting the cart between operating rooms. The cart will typically fit through standard operating room doors and onto standard hospital elevators. The cart should have a weight and wheel (or other transportation) system that allows the cart to be positioned adjacent an operating table by a single attendant. The cart should have sufficient stability in the transport configuration to avoid tipping at minor discontinuities of the floor, and to easily withstand overturning moments that will be imposed at the ends of the robotic arms during use.

Figure 3:
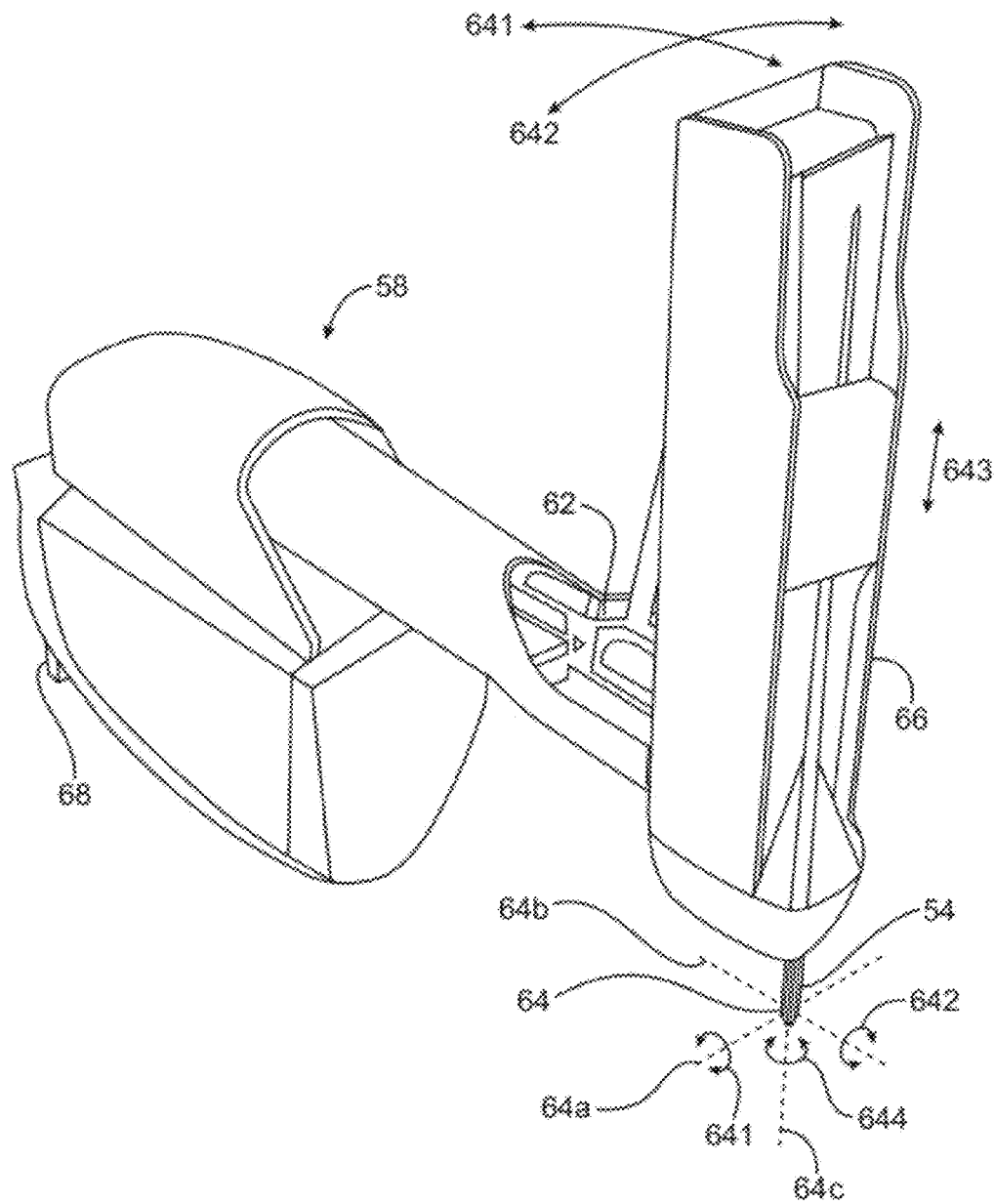
FIG. 3 illustrates a perspective view of a slave manipulator of a patient-side cart incorporating various aspects of the present invention.

FIG. 3 illustrates, as an example, a perspective view of one of the slave manipulators 58 included in the patient-side cart 50. Each of the slave manipulators 58 preferably includes a linkage 62 that constrains movement of a medical device 54. More specifically, linkage 62 includes rigid links coupled together by rotational active joints (i.e., rotated or moved by corresponding motors) in a parallelogram arrangement so that device 54 rotates around a point in space 64 (also referred to herein as the pivot point), as more fully described in issued U.S. Pat. No. 5,817,084, entitled "Remote Center Positioning Device with Flexible Drive," the full disclosure of which is incorporated herein by reference. The parallelogram arrangement constrains rotation (shown as two-headed arrow 641) to pivoting about an axis 64a, sometimes called the pitch axis. The links supporting the parallelogram linkage are pivotally mounted to setup joints in the positioning linkage 56 so that the medical device 54 further rotates (shown as two-headed arrow 642) about an axis 64b, sometimes called the yaw axis. The pitch and yaw axes intersect at the remote center 64, which is aligned along a shaft 66 of device 54.

The medical device 54 has still further driven degrees of freedom as supported by slave manipulator 58, including sliding motion (shown as two-headed arrow 643) of the tool along insertion axis 64c (the axis of shaft 66), sometimes referred to as insertion. As device 54 slides along axis 64c relative to slave manipulator 58, remote center 64 remains fixed relative to base 68 of the slave manipulator 58. Hence, the entire manipulator is generally moved to re-position the remote center or pivot point 64.

Linkage 62 of slave manipulator 58 is driven by a series of motors (not shown) which move respectively corresponding active joints in the manipulator 58. These motors actively move linkage 62 in response to commands from the processor of the surgeon console 150. Other motors (not shown) are coupled to the medical device 54 so as to rotate (shown as two-headed arrow 644) the device 54 about axis 64c, and often to articulate a wrist at the distal end of the device 54 (for example, when the device is a surgical instrument or tool) about at least one, and often two, degrees of freedom. Additionally, these device driving motors can be used to actuate an articulatable end effector of the device 54, for example to grasp tissues in the jaws of a forceps or the like, by being coupled to at least some of the joints of device 54 using cables, as more fully described in commonly owned U.S. Pat. No. 5,792,135, entitled "Articulated Surgical Instrument for Performing Minimally Invasive Surgery with Enhanced Dexterity and Sensitivity," the full disclosure of which is incorporated herein by this reference. As described in that patent, the manipulator 58 may include flexible members for transferring motion from the drive components to the surgical tool. For endoscopic procedures, the slave manipulator 58 may couple to a cannula (not shown), which may be releasably coupled to manipulator 58 and provide support to the medical device 54 so as to allow it to rotate and move axially through the central bore of the cannula.

Figure 4:
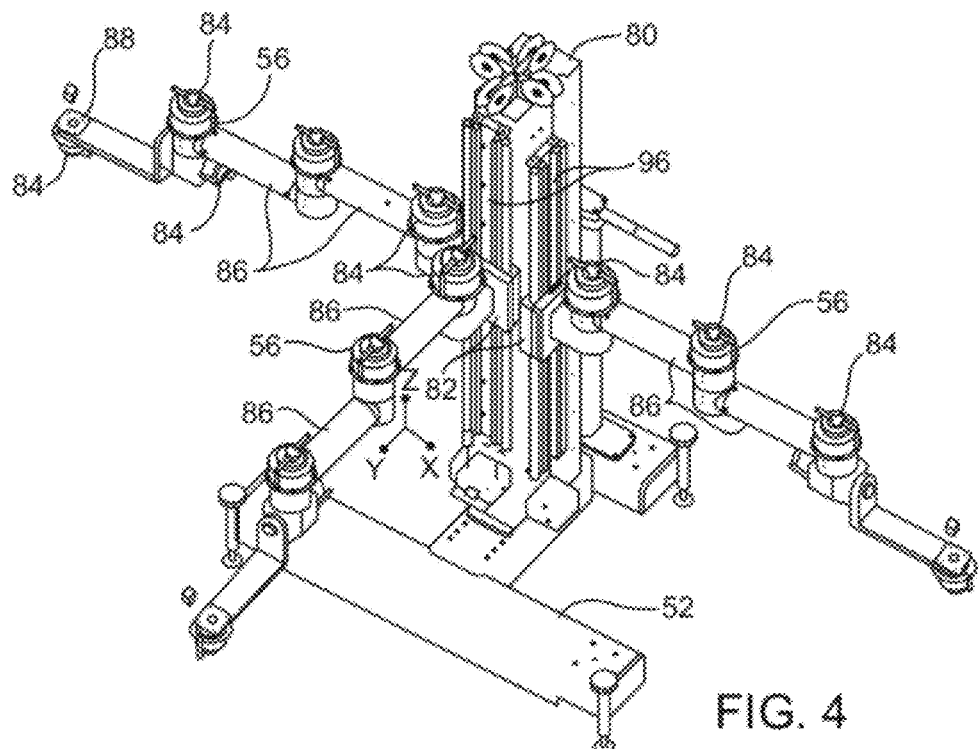
FIG. 4 illustrates a perspective view of a patient-side cart with exposed positioning linkages for supporting slave manipulators, utilizing aspects of the present invention.

FIG. 4 illustrates, as an example, a perspective view of the patient-side cart 50 with exposed positioning linkages 56 for supporting slave manipulators 58. The exemplary positioning linkage system includes three types of structures. First, a vertical column 80 supports vertically sliding joints 82 that are used to position the slave manipulators 58 along the vertical or Z-axis. Second, rotary setup joints 84 separated by rigid links 86 are used to horizontally position the slave manipulators 58 in the X-Y plane. Third, another series of rotary setup joints 84 mounted adjacent a manipulator interface 88 rotationally orients the slave manipulators 58.

Figure 5:
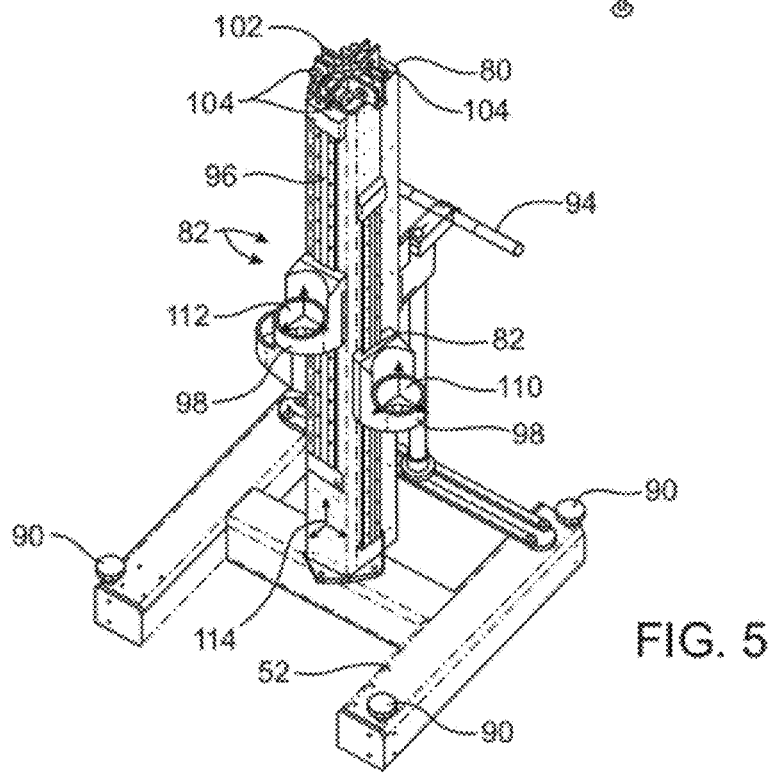
FIGS. 5~6 illustrate front and rear perspective views of a vertical structure of the patient-side cart incorporating various aspects of the present invention.
Figure 6:
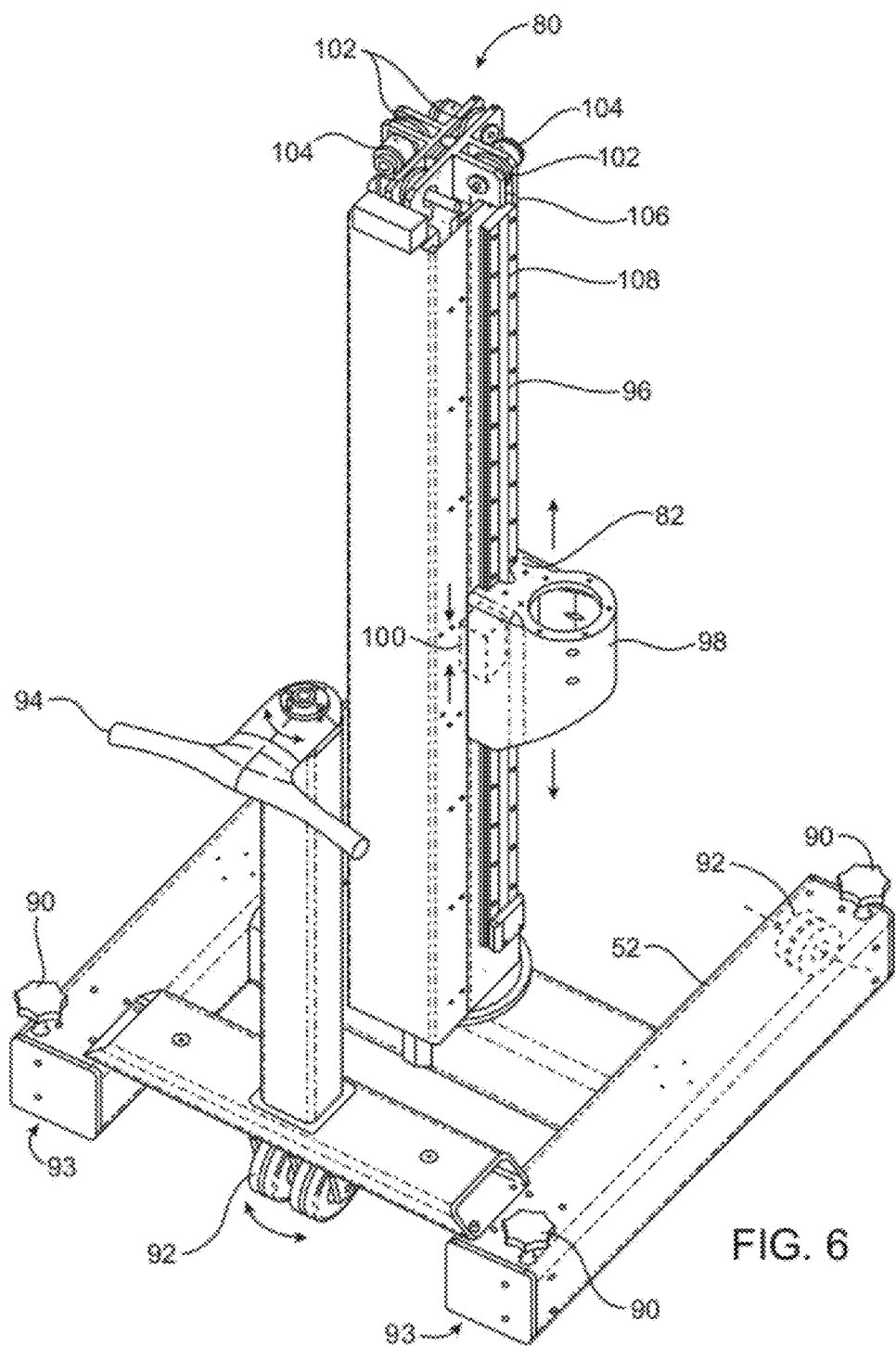

FIGS. 5-6 illustrate, as examples, front and rear perspective views of a vertical structure of the patient-side cart 50, including the column 80, vertical sliding joints 82, and base 52. The base 52 generally distributes the weight of the robotic arm structures and the forces imposed on the patient-side cart 50. When used for surgery, base 52 may be fixedly supported by a series of jacks 90 to avoid inadvertent movement of the robotic arms. Jacks 90 will typically be threadably coupled to the remainder of base 52, so that the jacks 90 can be retracted for transport. When jacks 90 are retracted by rotating their handles, base 52 rests on wheels 92.

To prevent the cart from tipping as it is rolled on wheels 92, the wheels located near the front of the cart will preferably be non-swiveling. In other words, the wheels will rotate about a fixed axis relative to the base 52. Wheels 92 adjacent a rear portion of the cart 50 will preferably be coupled to steering handle 94 so that the wheels and handle rotate about a steering axis. This facilitates maneuvering of the cart 50 and positioning of the cart 50 adjacent the operating table. To assist or otherwise facilitate movement of the cart, one or more motors may be included therein for such purpose.

As the weight of base 52 generally enhances the tipping stability of the slave cart structure, and as a box section enhances stiffness, the exemplary base 52 comprises box steel tubing, which may be welded or bolted together.

Column 80 extends upward from base 52, and may optionally also include a box steel structure. Sliding joints 82, including vertical tracks 96 on which sliders 98 ride, are counterbalanced by weights and/or springs 100 mounted within column 80. More specifically, a cable extends upward from slider 98 and over a pulley 102, and then down from the pulley to the weight and/or spring 100 within column 80. The weight and/or spring 100 preferably has a mass and/or provides an effective mass that is substantially equal to the combined mass of the slider 98, positioning linkage 56, slave manipulator 58, and medical device 54. This allows the robotic arms to be re-positioned upward or downward with very little effort. It should be understood that weight and/or spring 100 is schematically illustrated, and may have an actual length, position and dimension different than that as shown in the figure. Also, to determine stretching or retraction of the spring, a potentiometer may also be included as part of the block 100, which is provided for each robotic arm of the patient-side cart 50.

To prevent inadvertent movement of sliding joint 82, pulleys 102 are coupled to column 80 by brakes 104. These brakes 104 prevent rotation of the pulleys 102 when slider 98 is positioned.

As described above, it is often advantageous to identify the configuration of the joints of the patient-side cart 50 so as to allow the processor of the surgeon console 150 to perform coordinate transformations, calculate relative positions of surgical end effectors, and the like. Toward that end, sliding joints 82 include sensors 106 coupled to sliders 98 or counterweight assemblies 100 by cables 108. Sensors 106 comprise accurate potentiometers that generate electrical signals which vary with the position of sliders 98 along tracks 96. As the structure and position of sliding joints 82 relative to column 80 is known, knowing the axial position of sliders 98 allows the processor to perform transformations between first and second slider coordinate systems 110, 112 and a reference base coordinate system 114. Similarly, by knowing the angles defined by each rotary joint 84, transformations between the slider joints and a slave manipulator base can also be calculated. It should be understood that these interim coordinate system transformations need not be performed, but that they are representative of the total transformation to be performed. Regardless, where the configuration of all joints between the base 52 and the end effectors of medical devices 54 are known, the processor can accurately determine the position and orientation of the end effector, as well as how to effect movement in a desired direction by articulating one or more of the driven joints.

Each sensor preferably may comprise redundant potentiometers that "self-check" one another. That is, information from the redundant potentiometers may be compared with a selected tolerance to ensure to a degree of accuracy that the positioning of the corresponding joint is correctly known. If the information from the redundant potentiometers fail to match, the operator may be informed of this fact and/or the setup may be interrupted or delayed until corrective action is taken. Additionally, the operator may be able to override such an interrupt if desired. Potentiometers on the positional linkage 56 may be also checked for movement, to warn an operator of unintended movement of the normally locked and stationary positional linkages 56 during an operation, such as might be due to an assistant unintentionally leaning against the linkage.

Figure 7:
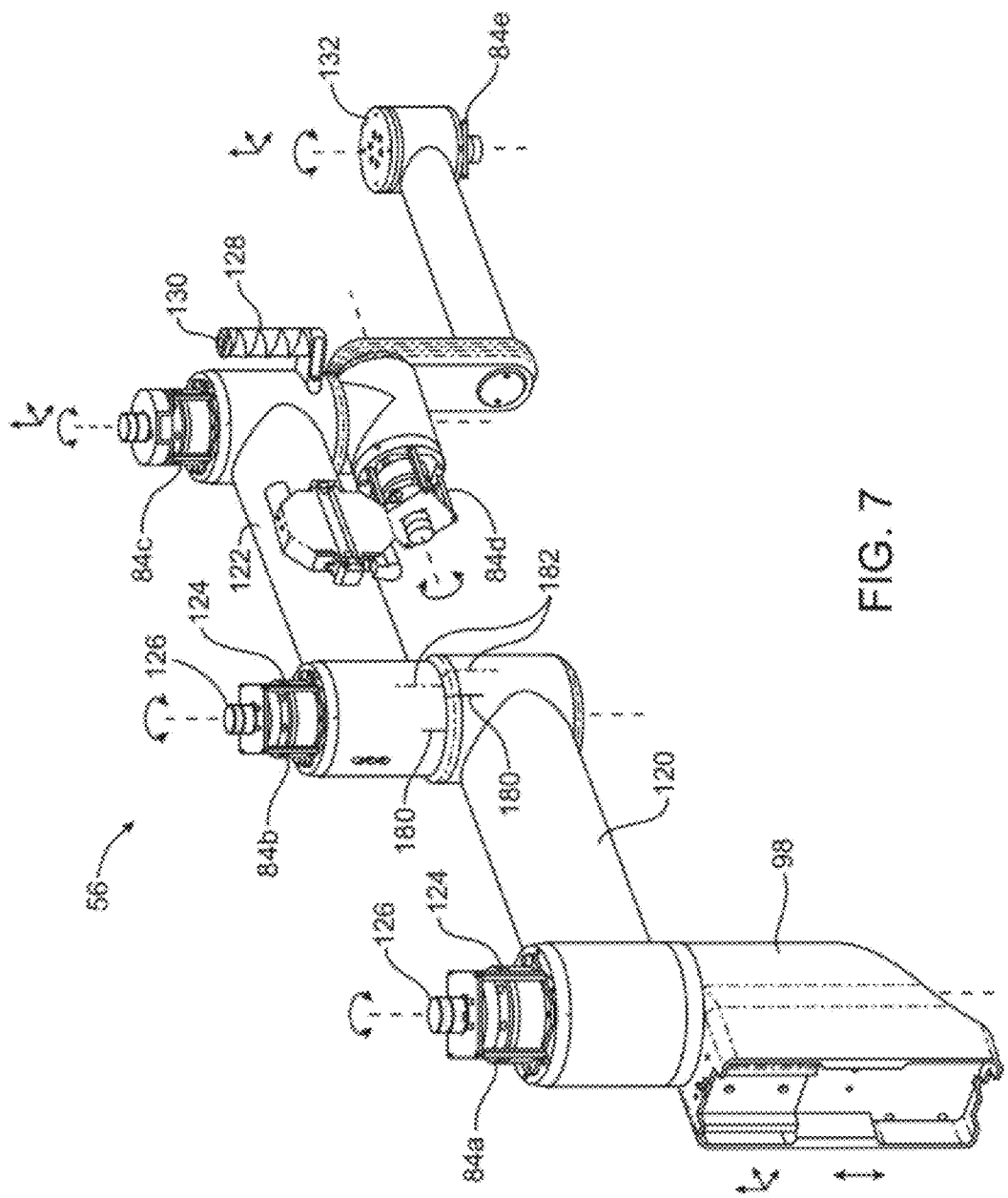
FIG. 7 illustrates a perspective view of a positioning linkage as part of a robotic arm included on a patient-side cart incorporating aspects of the present invention.

FIG. 7 illustrates, as an example, a perspective view of one of the positioning linkages 56. Positioning linkage 56 is supported by slider 98, and includes first and second elongate links 120, 122. First link 120 is coupled to slider 98 by rotational setup joint 84a, and is coupled to second link 122 by rotational setup joint 84b. As described above, slider 98 moves up and downward (along the Z-axis) to vertically position the slave manipulator 58 and remote center of rotation 64. Pivoting of the first and second linkages 120, 122 relative to the slider 98 and to each other allows the manipulator 58 to move horizontally (in the X-Y plane). As rotational setup joints 84a, 84b rotate about vertical axes, the height of the manipulator 58 does not change when these joints rotate and no counterbalancing is required.

Rotational setup joints 84a, 84b generally include corresponding brakes 124 and sensors 126. Each brake 124 prevents rotation about its corresponding joint unless the brake is released. In other words, the brake is normally on (so that the joint is in a fixed configuration). This prevents inadvertent articulation of positioning linkage 56 during a surgical procedure, and also avoids movement if power to the medical robotic system is lost. The brakes 124 may be safely overcome (so as to articulate the setup joints 84a, 84b without damage) with a reasonable amount of manual force against the linkage 56 or manipulator 58, thereby providing a safety feature if power is lost.

A wide variety of alternative brake structures could be used in place of the exemplary embodiment described above. Suitable brakes may be actuated electrically, pneumatically, hydraulically, or the like, and may be located at the joint axis (as shown) or may coupled to the setup joints 84a, 84b using gears, cables, rigid linkages, or the like.

Sensors 126 of setup joints 84a, 84b generate electrical signals which indicate the rotational angle defined by the joints. Sensors 126 preferably generate absolute angle indication signals that vary with the absolute angle defined by the setup joints, rather than generating a signal which indicates a change in the angle.

This avoids having to regularly return the setup joints 84a, 84b to a zero position to provide an accurate angle measurement. Although absolute angle measurement devices are generally preferred, in some embodiments sensors 126 may comprise encoders that measure a number of discrete changes in the setup joint angle, or a wide variety of alternative structures.

Links 120 and 122 may be formed of a wide variety of high strength, light weight materials. Alternative structures might include aluminum or composites, such as graphite or the like. In general, minimizing the weight of the robotic arm structures can dramatically decrease the total weight of the patient-side cart 50, as the structures are often counterbalanced and any added weight generally increases the cart base weight to avoid tipping.

Positioning of the slave manipulator 58 in preparation for surgery may be facilitated by providing a handle 128 affixed to the distal end of second link 122. Handle 128 has an actuation button 130 that releases brakes 124 so as to allow movement of the setup joints 84a, 84b and consequently, the positioning linkage 56. As described above, the setup joints 84a, 84b will preferably remain locked unless a signal is provided by circuitry coupled to actuation button 130. Affixing handle 128 on or near the manipulator support interface allows the positioning linkage 56 to be moved without imposing undue forces against the servomechanism of the manipulator structure.

In addition to the positional capabilities of positioning linkage 56, rotational active joints 84c, 84d, 84e allow the manipulator 58 to be rotated to a desired orientation. Including the vertical adjustability provided by sliding joint 82, positioning linkage 56 allows the manipulator 58 to be positioned with six degrees of freedom relative to base 52 of the patient-side cart 50. As illustrated, one or more orientational degrees of freedom may be provided between an operator manipulated input device of the surgeon console 150 and the slave manipulator 58. As each of the rotational setup and active joints 84a-84e and the sliding joint 82 include a sensor coupled to a processor of the medical robotic system, the processor can calculate a position and orientation of a manipulator interface 132 on which the manipulator 58 is mounted, and can also perform the coordinate system transformations described hereinabove.

In the exemplary embodiment, the brakes 124 at all of the joints on one of the three positioning linkage 56 supporting a slave manipulator 58 are actuated in unison by actuation button 130 on handle 128, allowing the operating room personnel to position and orient the manipulator 58 freely. The manipulator 58 will preferably be balanced about rotational active joints 84d, 84e, as these joints may rotate about axes that are at an angle from vertical. Fabricating the manipulator 58 or adding counterbalance weights to the manipulator 58 so that the center of mass of the manipulator 58 is aligned along the axes of rotation of these two joints will prevent the operating room personnel from having to overcome a righting moment when rotationally positioning the manipulator 58.

Figure 8:
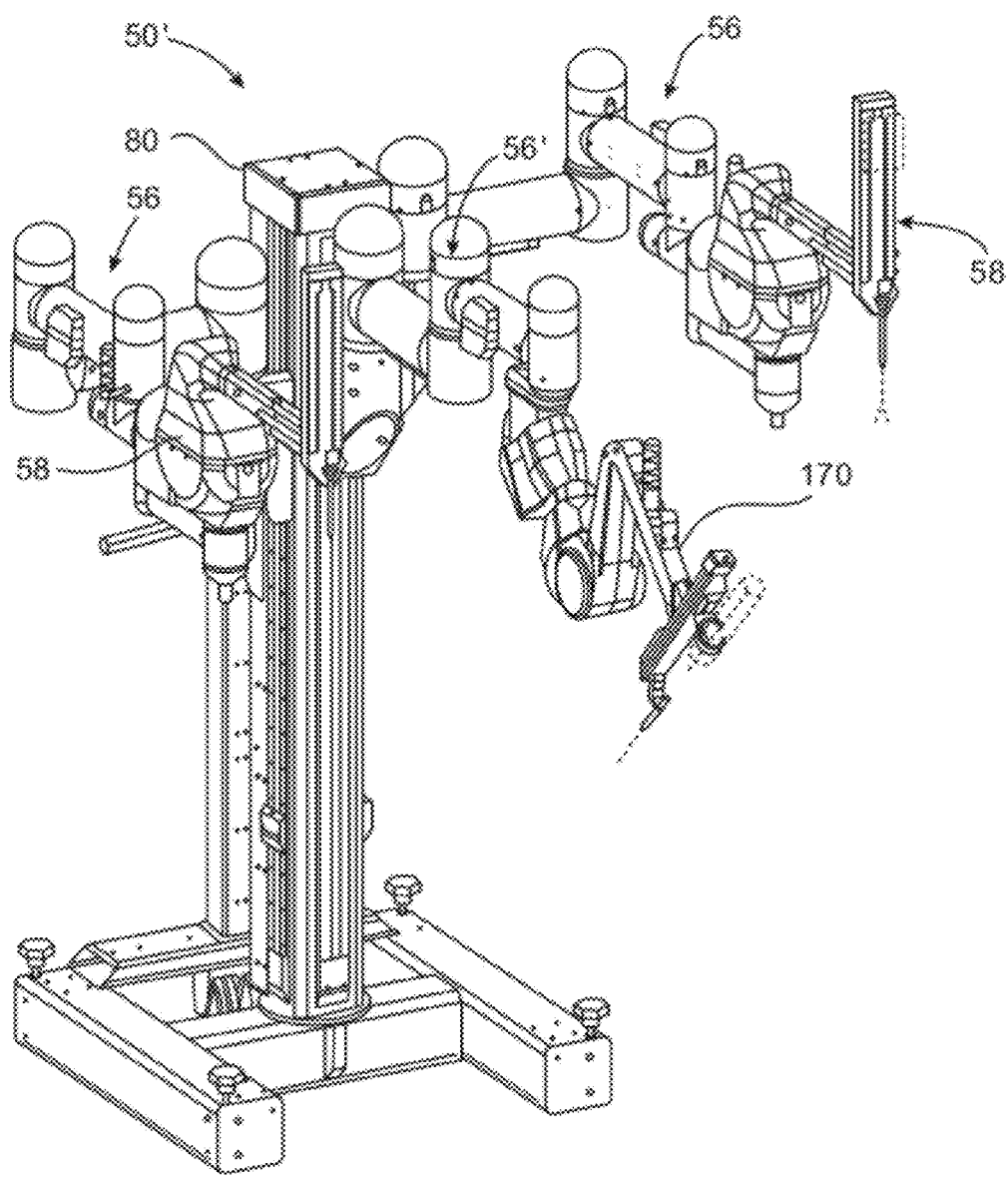
FIG. 8 illustrates a perspective view of a patient-side cart with robotic arms holding medical devices including a modified middle arm for holding and positioning an endoscope, utilizing aspects of the present invention.

FIG. 8 illustrates, as an example, a perspective view of an alternative patient-side cart 50' with robotic arms holding medical devices including a modified middle arm for holding and positioning an endoscope. The cart 50' includes a positioning linkage 56' with less than six degrees of freedom, supported between two six degrees of freedom positioning linkages 56 (such as previously described). Six degree of freedom linkages 56 generally extend radially outwardly from column 80 and will often be arranged to support the medical devices 54 (including the tissue manipulating tools and the endoscope), so that the elongated shafts of these endoscopic instruments extend radially outwardly from a pattern of apertures into an internal surgical sites, as illustrated in FIG. 1. This gives the cart system 50' an "elbows out" appearance in use, which helps enhance the clearance between the slave manipulators 58 so as to avoid collisions as the manipulators 58 move in the space over patient P during a surgical procedure. An endoscope manipulator 170 and its associated linkage 56' will often be arranged so as to extend substantially from column 80 to the endoscope, as also illustrated in FIG. 1. Endoscope manipulator 170 may not include all of the tool actuation drive system provided for articulated surgical instruments, which are typically included in manipulators 58. An exemplary endoscope manipulator 170 is more fully described in commonly owned U.S. Pat. No. 6,451,027 entitled "Devices and Methods for Moving an Image Capture Device in Telesurgical Systems," the full disclosure of which is incorporated herein by reference.

Figure 10:
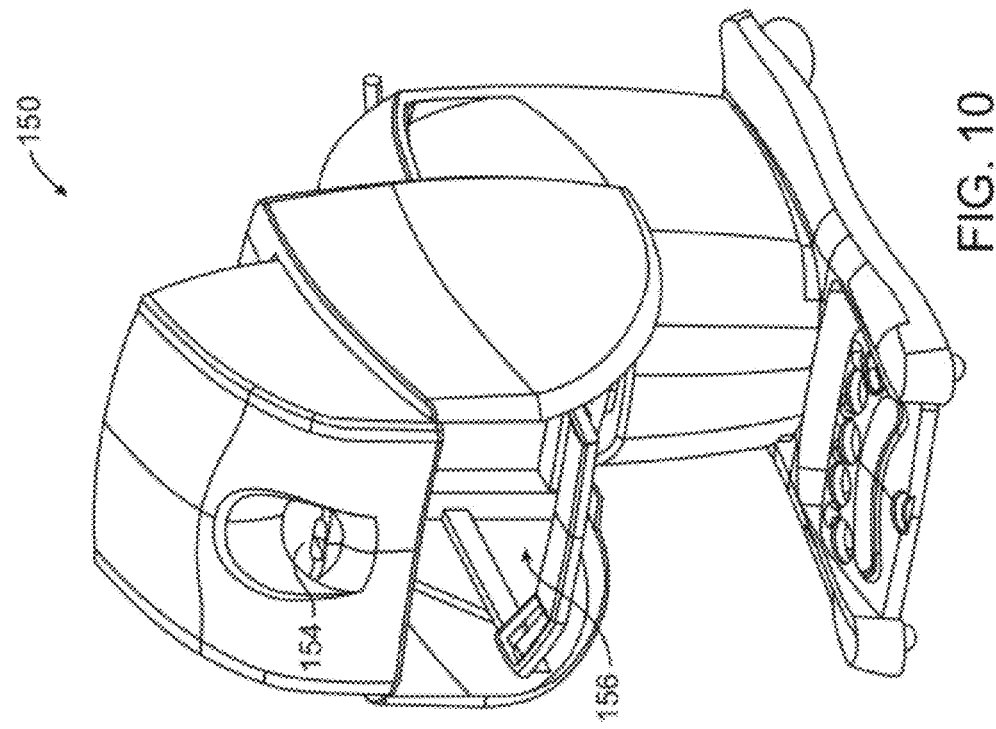
FIGS. 9~10 illustrate rear and front perspective views of a surgeon console included in a medical robotic system, utilizing aspects of the present invention.
Figure 9:
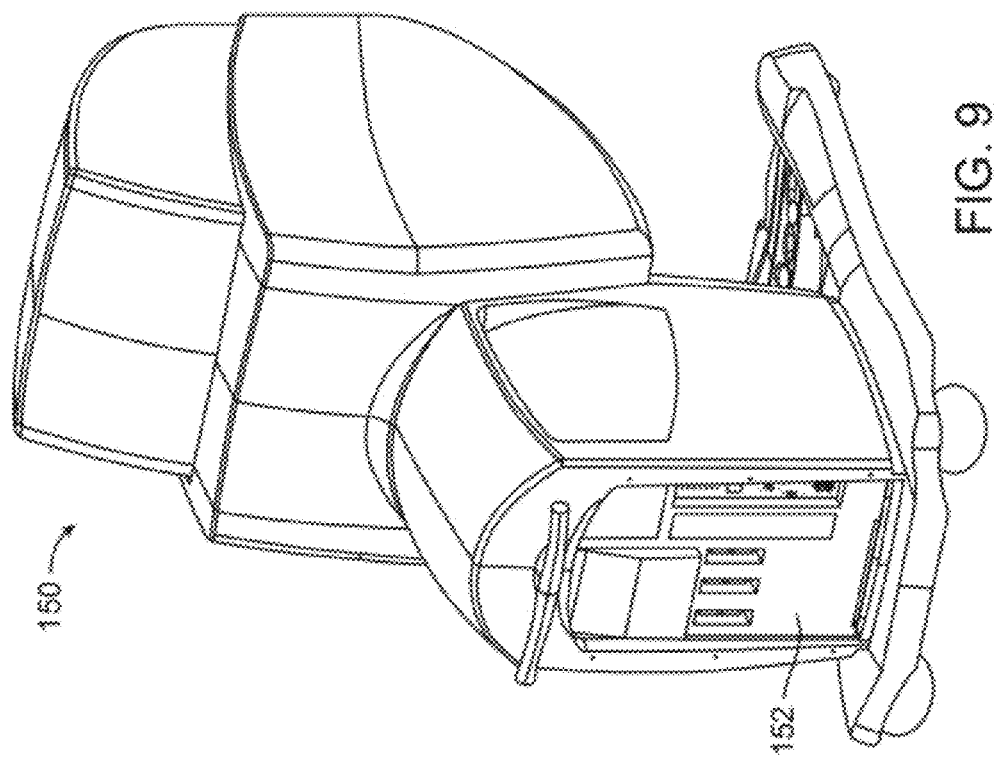

FIGS. 9~10 illustrate, as examples, rear and front perspective views of the surgeon console 150. The surgeon console 150 includes one or more processors 152 for the robotic servomechanism. Also included in surgeon console 150 are a stereo imaging system 154 and a pair of master input devices or controllers 156, which hang below the imaging system 154.

The surgeon will generally manipulate tissues using the medical robotic system by moving the input devices 156 within a three dimensional input device workspace of the surgeon console 150. In the exemplary embodiment, the surgeon will manipulate these input devices 156 while viewing the surgical site through display 154. Processor 152 can calculate an image capture coordinate system via the sensors in positioning linkage 56' and manipulator 58 supporting the endoscope, and can perform coordinate system transformations so as to generate signals to the manipulator structure that maintain alignment between the three dimensional image of the end effector as viewed through display 154 and the input devices 156 within the input device workspace. By maintaining this alignment as the physician moves the input devices 156 in both position and orientation, the medical robotic system allows the surgeon to manipulate the medical tools as if each of the input devices 156 in the surgeon's hands and their corresponding end effector in the surgeon's field of view define a single contiguous medical tool 54. This provides an enhanced sense of presence and allows the surgeon to operate efficiently and accurately without performing mental coordinate transformations. The correlation between movement of the input devices 156 and image of the end effector is more fully described in U.S. Pat. No. 5,808,665 entitled "Endoscopic Surgical Instrument and Method for Use," while an exemplary method and structure for performing the coordinate system transformation calculations is detailed in commonly owned U.S. Pat. No. 6,424,885 entitled "Camera Referenced Control in a Minimally Invasive Surgical Apparatus", the full disclosures of which are incorporated herein by reference.

Figure 11:
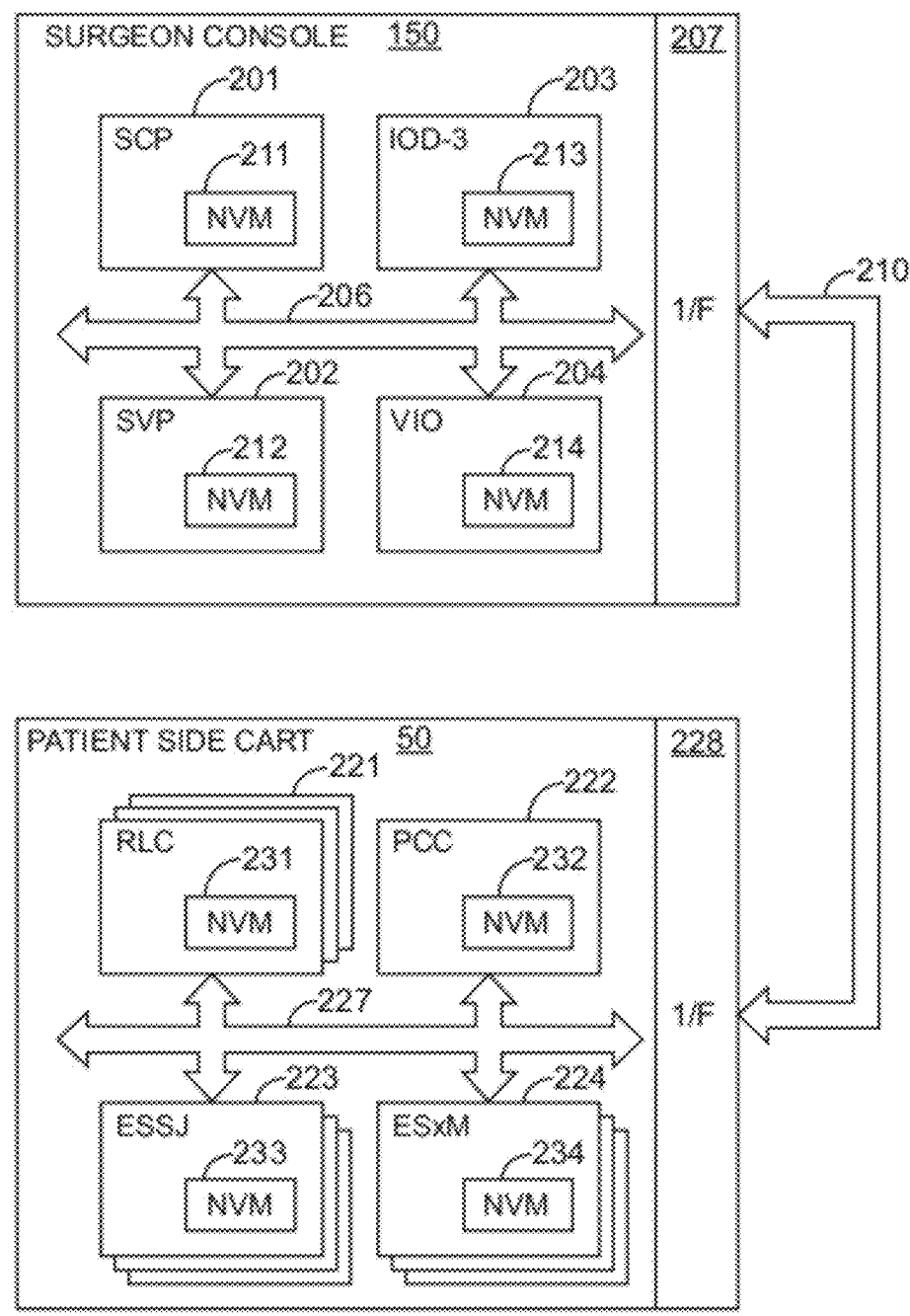
FIG. 11 illustrates a block diagram of printed circuit assemblies included in a surgeon console and patient-side cart, utilizing aspects of the present invention.

FIG. 11 illustrates, as an example, a block diagram of exemplary Printed Circuit Assemblies (PCA's) included in the surgeon console 150 and the patient-side cart 50. Hierarchically, the surgeon console 150, the patient-side cart 50, and the PCA's may be considered as subsystems of the medical robotic system. The PCA's may also be considered as subassemblies of the surgeon console 150 and/or the patient-side cart 50. Other mechanical, electrical, and electro-mechanical components of the medical robotic system may also be considered subsystems of the medical robotic system or subassemblies of their respective subsystems, such as the positioning linkages 56 and slave manipulators 58 of the robotic arms, the setup joints 84a, 84b and their respective release brakes 124 of the positioning linkages 56, the active joints 84c, 84d, 84e and their respective motors of the slave manipulators 58, and the Z-axis springs 100 used to dampen and/or counterbalance movement of their respective robotic arms in the vertical direction during their setup.

A System Control Processor (SCP) PCA 201, I/O Distribution (IOD-3) PCA 203, System Video Processor (SVP) PCA 202, and Video I/O Processor (VIO) PCA 204 are included in the surgeon console 150, and located in its card cage. Although not shown, a number of Video Processing Daughter VPD) PCA's may also be plugged into the SVP PCA 202 for use by the vision subsystem.

The SCP PCA 201 serves as the master controller for the surgeon console 150, and performs supervisory functions for the entire medical robotic system. Multiple processors may be included on this PCA serving as compute engines for the master input devices (also referred to as "master manipulators"). The IOD-3 PCA 203 serves as an interface to all external Input/Output (I/O) to the internal system electronics. It also performs some pre-processing of incoming encoder data as well as some power fault monitoring. The SVP PCA 202 serves as the master controller for the vision subsystem, and interfaces the vision cart (including the assistant display 12) to the surgeon console 150. The VIO PCA 204 and VPD daughter PCA's are used by the vision system. Remote arm Logic Controller (RLC) PCA's 221 (one for each robotic arm), a Patient-side Cart Controller (PCC) PCA 222, Embedded Serializer Setup Joint (ESSJ) PCA's 223 (one for each robotic arm), and Embedded Serializer Manipulator (ESxM) PCA's 224 (one for each robotic arm) are included in the patient-side cart 50. The RLC PCA's 221 and the PCC PCA 222 are located inside the base 52 of the patient-side cart 50. The ESSJ PCA's 223 are located near the setup joints of their respective robotic arms, and the ESxM PCA's 224 are located near the extremities of their respective robotic arms.

Each of the RLC PCA's 221 includes a Remote Compute Engine (RCE) and serves as master controller for its respective robotic arm performing supervisory functions and controlling booting of its respective RCE, and the ESSJ and ESxM processors of its respective ESSJ and ESxM PCA's 223 and 224. The PCC PCA 222 serves as master controller for the patient-side cart 50. In particular, it controls power to the cart side controllers, performs supervisory functions, and manages the cart motion and battery control functions. Each of the ESSJ PCA's 223 gathers motor and sensor data from the setup joint motors (or brakes) of its respective robotic arm, and sends the data to its associated RLC PCA 221. Similarly, each of the ESxM PCA's 224 gathers motor and sensor data from the active joint motors of its respective robotic arm, and sends the data to its associated RLC PCA 221.

Communication between PCA's in the surgeon console 150 is facilitated by local bus 206, communication between PCA's in the patient-side cart 50 is facilitated by local bus 227, and communication between PCA's in the surgeon 150 and PCA's in the patient-side cart 50 is facilitated by a system bus 210 in conjunction with bus interfaces 207 and 228 respectively on the surgeon console 150 and patient-side cart 50. System bus 210 also supports communications to and from the vision cart.

Each of the PCA's includes logic circuitry to perform its designated functions, and at least one non-volatile memory to store usage-related and other maintenance information for the PCA, as well as, in some cases, for its associated subsystems and subassemblies. The maintenance information may include service events and dates so that a complete service history (including other useful service related information such as an identification of the party performing the service, problems encountered while performing the service, reason for the service, etc.) is available for and travels with the system, subsystem, subassembly, and/or other component associated with the non-volatile memory. Also stored in the non-volatile memory is an identification of the component for which the usage-related information is to be associated, such as a unique serial number of the component. As used herein, the term "component" is to be understood to include a subsystem of the medical robotic system, or a subassembly of the subsystem, or a component of the subassembly.

The usage-related information is stored primarily for preventive maintenance purposes. Examples of such usage-related information include a time that power is up (i.e., powered on) for the component, a cycle count of a number of times that the component is powered up and down (i.e., powered on and off), a measure of time since installation of the component, a measure of time since the last preventive maintenance for the component was performed, a count of the number of medical procedures that have been performed used the component, and an accumulated period of time that the component has been electrically conducting (i.e., power-on or battery run time). Where the component being monitored is one of the Z-axis springs 100, the usage-related information may include a count of a number of direction changes in the Z-axis for the Z-axis spring 100 (i.e., in the vertical up and down directions). Multiple regions or zones in the Z-axis direction may be defined and counts recorded for movement therein (e.g., direction changes) of the Z-axis spring in order to accommodate more sophisticated usage threshold algorithms. For the measure of time since installation of a component or last preventive maintenance for the component, the measurement may be in terms of days starting from the calendar date of the installation or preventive maintenance, which is stored in such case in the associated non-volatile memory of the component along with a serial number or other identifying indication of the component.

In addition to preventive maintenance purposes, the usage-related information stored in non-volatile memory may also be used for failure analysis purposes when the memory travels with the failed component. This solves a very tough logistical problem that is presented when the manufacturer's quality and reliability organization tries to piece the life story of the failed component together when it has been installed in multiple systems since it was built.

Figures 12, 13:
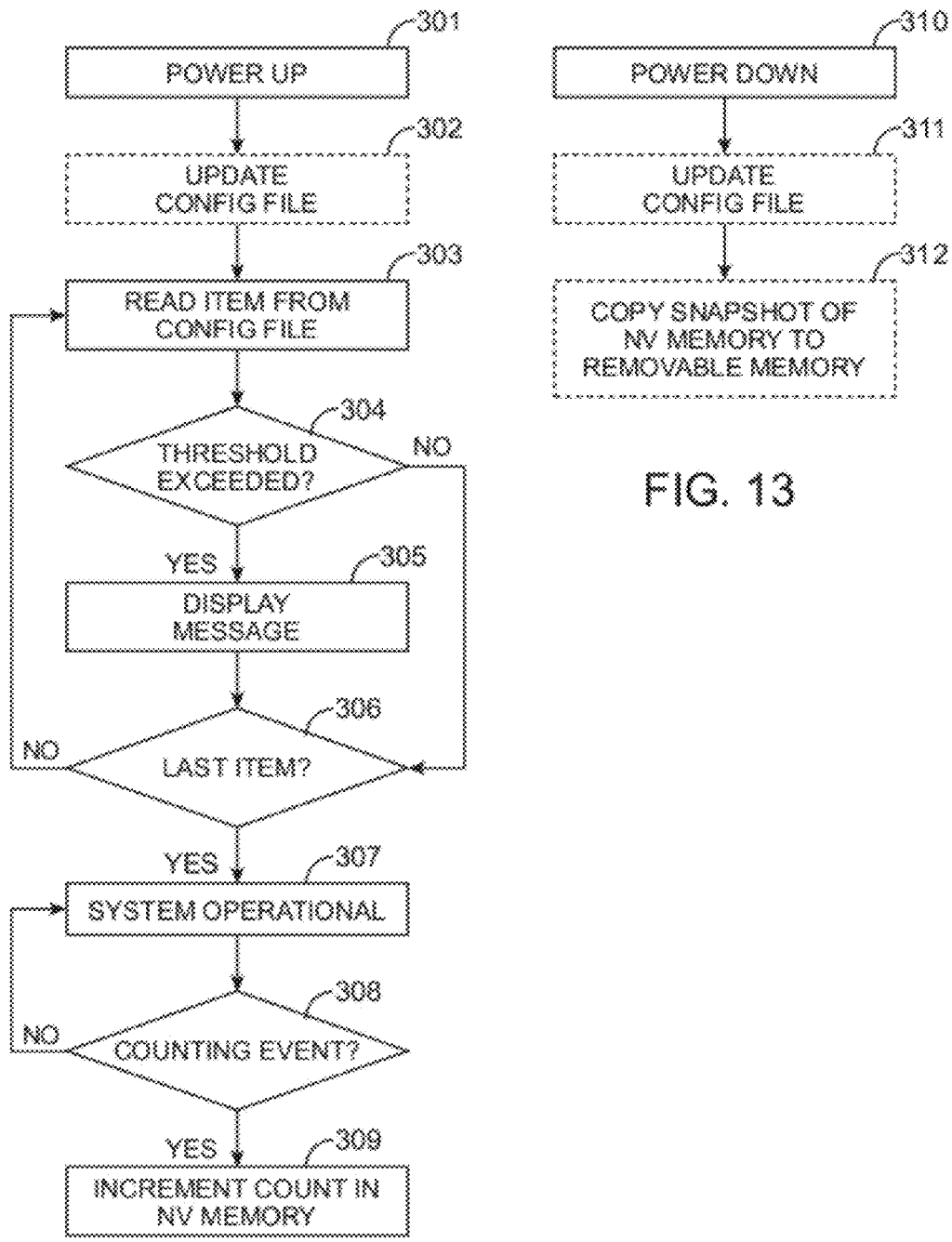
FIG. 12 illustrates a flow diagram of a preventive maintenance method utilizing aspects of the present invention.
FIG. 13 illustrates a flow diagram of a method used for performing optional power down tasks in conjunction with a preventive maintenance method utilizing aspects of the present invention.

FIG. 12 illustrates a flow diagram of a preventive maintenance method utilizing the usage-related information stored in non-volatile memories of the medical robotic system, such as the non-volatile memories (NVM) 211~214, 231~234 of PCA's 201~204, 221~224. In 301, the system is first powered up. Upon being powered up, optionally, in 302, a system configuration file is updated with the usage-related information stored in the non-volatile memories associated with the monitored components, such as counts for elapsed time measurements and calendar dates for installation of the components or preventive maintenance previously performed on the components along with serial numbers or other identifying indicia of the components. The updating in this case is performed by a processor on the SCP PCA 201, and the system configuration file is preferably stored in the NVM 211 of the SCP PCA 201. Optionally, the updating of the system configuration file may also or alternatively be performed at power down of the system as shown in 311 of FIG. 13. In this latter case, although it may not be necessary to perform 302 in addition to performing 311, it would be useful to perform the system configuration file update at both power up and power down in order to determine if any changes have been made to the system such as replacement of components of the medical robotic system since the last time power was turned on.

In 303~306, selected ones of the items of usage-related information stored in the system configuration file are checked by the processor in the SCP PCA 201 to determine whether these items have exceeded predetermined threshold limits. In the preferred embodiment, each selected item may be checked for two threshold limits. Exceeding the first threshold, results in issuing an error message on the display screen of the surgeon console 150. Even though the first threshold is not exceeded, exceeding the second (and lower) threshold, results in issuing a warning message on the display screen of the surgeon console 150.

Thus, in 303, a selected item is read from the system configuration file, and in 304, the item is checked to see if it exceeds either the first or second threshold. If no threshold is exceeded, then in 306, it is determined whether the item currently being processed is the last item to be checked. If it is the last item, then the method proceeds to 307 so that the system is ready to perform a medical procedure. On the other hand, if it is not the last item, then the next item to be checked is processed by jumping back to 303.

If either the first or second threshold limit is determined to be exceeded for the item in 304, then in 305, an appropriate message is displayed on the display screen of the surgeon console 150. For example, if the first threshold limit is exceeded, an error message such as "Non-recoverable fault: XXXXX. Contact Customer Service," may be displayed where XXXXX indicates the type of error, and if the second threshold limit is exceeded, a warning message such as "Preventive Maintenance recommended. Contact Customer Service," may be displayed. In addition to displaying the error message, the system may also be locked or otherwise transitioned to an error state so that medical procedures may not be performed using the medical robotic system until the indicated preventive maintenance is performed, following which, a field service technician may reset the counts or increment the usage thresholds. Although only one warning threshold is described herein, it is to be appreciated that several warning threshold levels may be employed with each subsequent warning indicating a stronger worded recommendation that preventive maintenance be performed. In addition to the recommendation that preventive maintenance be performed, an estimate to a time when an error threshold that would shut the system down or lock it up may also be calculated and provided in the warning message.

In 307-309, the medical robotic system is operational (i.e., ready to perform a medical procedure), and selected processors on the PCA's perform the following tasks. In 307, a timer for each of the monitored components is started when power to the component is turned on (and stopped when the power to the component is turned off, with elapsed time recorded in the associated non-volatile memory), and in 308, each of the monitored components is monitored to identify when a counting event occurs. If a counting event is detected, then in 309, a count corresponding to the event is incremented in the associated non-volatile memory. In addition, an events list may also be updated in the non-volatile memory and/or the system configuration including an identification of the event that resulted in the count being incremented and the date or time of the incrementing.

Examples of counting events and usage threshold include the following for different items or usage-related information. When the usage is a measure of time starting from some event such as power up, installation, last preventive maintenance, or time of electrically conducting for a component, the counting event may be an elapsed period of time such as every five minutes starting from such an event, and the usage threshold may be a certain number of such counts indicating when preventive maintenance should be performed for such usage. When the usage is a cycle count of a number of times that the component is powered up and down, the counting event may be the detection of a power down request, and the usage threshold may again be a certain number of such counts indicating when preventive maintenance should be performed. When the usage is a count of the number of medical procedures that have been performed used the component, the counting event may be a surgeon generated indication that a medical procedure is to be performed, and the usage threshold may again be a certain number of such counts indicating when preventive maintenance should be performed. When the usage is a count of a number of direction changes for the Z-axis spring, the counting event may be a filtered output of a potentiometer measuring the movement of the spring in the Z-axis direction, and the usage threshold may again be a certain number of such counts indicating when preventive maintenance should be performed. The filtering in this last case is performed in order to eliminate vibrations on the spring that are not a result of a repositioning of its corresponding robotic arm.

The non-volatile memories 211~214, 231~234 of PCA's 201~204, 221~224 may be electrically programmable read-only-memory (EPROM) devices, electrically erasable and programmable read-only-memory (EEPROM) devices, or flash electrically erasable and programmable read-only-memory (flash EEPROM) devices. Since flash EEPROM devices do not generally support erasure of single bits, but require that all bits of the device be erased at the same time, it is desirable when using this kind of non-volatile memory to increment counts stored therein without having to erase any bits. One way to do this is using a simple "tick" scheme, wherein N bits are allocated to facilitate counting to N (i.e., one bit per count). Using this scheme, the N bits are initially erased so that they all indicate a "0" logic state, and each time the count is incremented, one of the N bits is changed to indicate a "1" logic state.

FIG. 13 illustrates, as an example, a flow diagram of a method used for performing optional power down tasks in conjunction with the preventive maintenance method described in reference to FIG. 12. In 310, a power down process is initiated for the medical robotic system. At this time, any timers started in 301 of FIG. 12 are stopped, and their elapsed times recorded in associated non-volatile memories. As previously described, in 311, the system configuration file is optionally updated with the usage-related information stored in the system non-volatile memories such as non-volatile memories 211~214, 231~234 of PCA's 201~204, 221~224. In addition, optionally, in 312, a snapshot of the contents of the system non-volatile memories or the system configuration file may be stored in a removable memory unit or device such as a PCMCIA or other format memory card.

Figure 14:
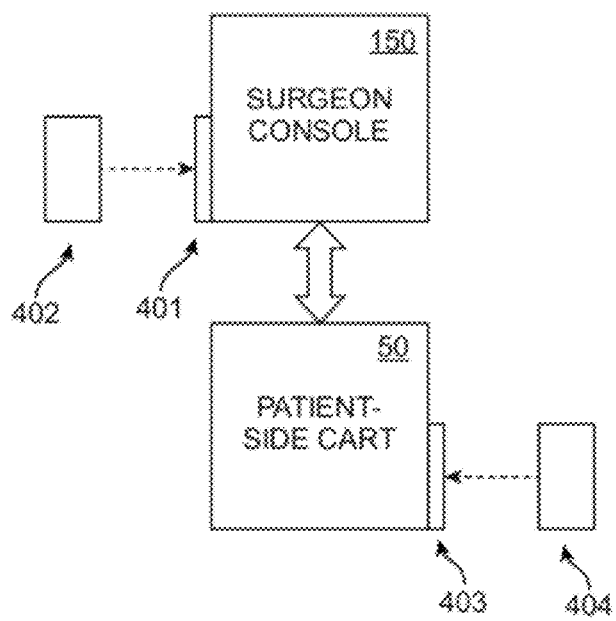
FIG. 14 illustrates a block diagram of a medical robotic system including a surgeon console and patient-side cart having removable memory units, utilizing aspects of the present invention.

FIG. 14 illustrates, as an example, a block diagram of a medical robotic system including a surgeon console 150 having a memory card slot 401 for inserting memory cards 402 such as a Sandisk CompactFlash® card distributed by Sandisk Corporation of Sunnyvale, Calif. In this case, the processor on the SCP PCA 201 may cause a snapshot of the contents of the non-volatile memories in both the surgeon console 150 and the patient-side cart 50 to be stored in the memory card 402 at power down. It may also cause the contents of the system configuration file to be stored instead or additionally in the memory card 402.

The medical robotic system also includes a patient-side cart 50 optionally having one or more memory card slots 403 for inserting memory cards 404 such as the aforementioned Sandisk CompactFlash® card. When only one memory card slot is provided, the slot may be located on the vertical column or base of the cart 50. In this case, the processor on the PCC PCA 222 may cause a snapshot of the contents of selected non-volatile memories in the patient-side cart 50 to be stored in the memory card 404 at power down. When a memory card slot is provided on each of the robotic arms of the patient-side cart 50, however, then the processor in either the ESSJ PCA 223 or ESxM PCA 224 associated with a robotic arm may cause a snapshot of the contents of selected non-volatile memories associated with the robotic arm to be stored in its inserted memory card at power down.

The description above has been primarily directed towards determining when preventive maintenance warnings and/or error messages should be displayed on a display screen of the surgeon console 150, and displaying those determined warnings and/or error messages at system start-up or power on. In addition to such a preventive maintenance method as described above, the present invention is also useful for reporting back the stored usage-related information to manufacturer's central office in order to forecast service resource needs to better support its customers, and service revenues for better financial planning.

Figure 15:
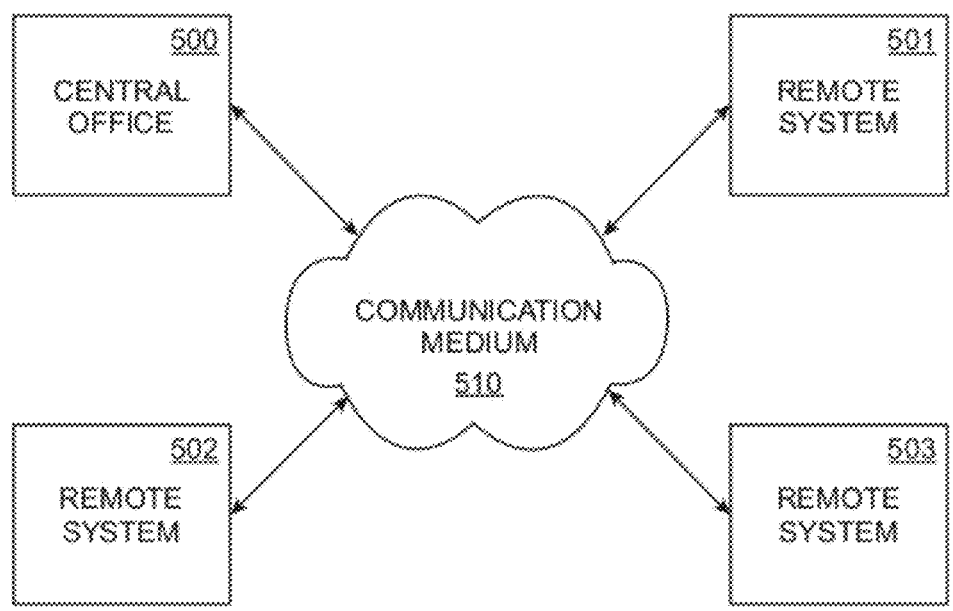
FIG. 15 illustrates a block diagram of a system for centrally processing usage-related information from a number of remote medical robotic systems for preventive maintenance forecasting and other purposes, utilizing aspects of the present invention.

FIG. 15 illustrates, as an example, a block diagram of a system for centrally processing usage-related information from a number of remote medical robotic systems for preventive maintenance forecasting and other purposes. In this example, remote medical robotic systems 501~503 communicate contents of their respective system configuration files back to a central office computer 500 through a communication medium 510 such as the Internet or direct telephone lines. Although only three medical robotic systems are shown in this figure, it is to be appreciated that the actual number may be significantly more, or even less. Transmission of the information may be performed upon power up or power down of the medical robotic systems 501~503, or such transmission may be performed at a programmed time of day or upon request by central office computer 500.

Figure 16:
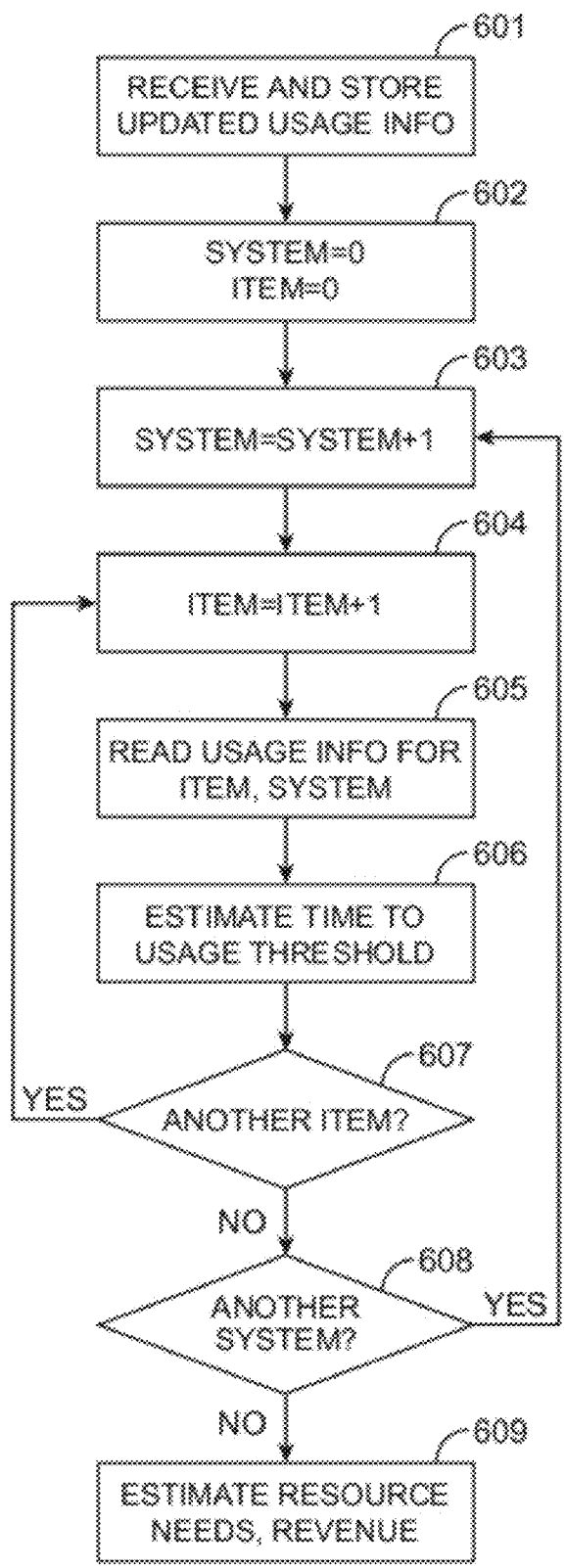
FIG. 16 illustrates a flow diagram of a method for monitoring preventive maintenance needs for a plurality of medical robotic systems, utilizing aspects of the present invention.

FIG. 16 illustrates, as an example, a flow diagram of a method performed by the central office computer 500 for monitoring preventive maintenance needs for remote medical robotic systems assigned to it. In 601, the central office computer 500 receives and stores updated usage-related information from the system configuration files of the medical robotic systems. The receipt of this information may occur as each of the medical robotic systems are powered on or powered off, or it may be received at designated times of the day or upon request by the central office computer 500, or it may be received upon the occurrence of some other event.

After the usage-related information is received and stored in a mass memory device of the central office computer 500, the central office computer 500 may perform tasks 602~609 to estimate preventive maintenance resource needs for the medical robotic systems and/or estimated service revenues from preventive maintenance to be performed on them.

In 602~604, parameters SYSTEM and ITEM are initialized for counting purposes in a conventional programming manner. The SYSTEM parameter in this case indicates one of the remote medical robotic systems, and the ITEM parameter indicates one of the usage-related items stored in the system configuration file for that SYSTEM.

In 605~606, usage-related information for a current ITEM and SYSTEM is read from memory, and processed to determine an estimated time to reach a usage threshold for the ITEM and SYSTEM. The estimation performed in 606 may be simply an extrapolation of several instances of such usage-related information taken at different times. For example, if the count for the ITEM is increasing at an average rate of 5 counts per day, then an estimate of the number of days that it would take to reach a usage threshold of 100 counts would be 20 days. More sophisticated estimation techniques may also be used for better results.

Conditional elements 607 and 608 cause the method to loop through all ITEMS for all SYSTEMS. The estimated preventive maintenance resource needs and revenue may then be determined in 609 by processing the estimated times to reach the usage thresholds as determined by the method looping through 603~608 as indicated, and applying appropriate preventive maintenance charges for each ITEM and SYSTEM according to their maintenance contracts.

Although the various aspects of the present invention have been described with respect to a preferred embodiment, it will be understood that the invention is entitled to full protection within the full scope of the appended claims.

We claim:

1. A preventive maintenance method for a medical robotic system, comprising:
    storing usage-related information for components of the medical robotic system in non-volatile memories respectively associated with the components, wherein the components include subsystems, and wherein the non-volatile memories reside in their respectively associated subsystems;
    determining whether one or more usage thresholds for the components are exceeded according to the stored usage-related information; and
    displaying messages on a display screen of the medical robotic system identifying individual of the components to be recommended for preventive maintenance based upon such determination of whether one or more usage thresholds for the components are exceeded.

2. The preventive maintenance method according to claim 1, wherein the subsystems include a patient-side unit and a surgeon console.

3. The preventive maintenance method according to claim 2, wherein the subsystems include a first plurality of slave manipulators included in the patient-side unit, and a second plurality of master manipulators included in the surgeon console.

4. The preventive maintenance method according to claim 2, wherein the subsystems include a first plurality of removable subassemblies included in the patient-side unit, and a second plurality of removable subassemblies included in the surgeon console.

5. The preventive maintenance method according to claim 4, wherein the first plurality of removable subassemblies includes a first plurality of printed circuit assemblies and a battery.

6. The preventive maintenance method according to claim 5, wherein the patient-side unit includes a plurality of robotic arms adapted to hold and manipulate medical devices, and individual of the plurality of robotic arms includes a plurality of setup joints for setting up the robotic arm so that its held medical device is manipulatable about a pivot point and a plurality of active joints for manipulating the robotic arm so as to manipulate its held medical device about the pivot point.

7. The preventive maintenance method according to claim 6, wherein the individual of the plurality of robotic arms further includes a first plurality of motors for breaking corresponding of the plurality of setup joints of the robotic arm, and the first plurality of printed circuit assemblies includes a first printed circuit assembly for gathering setup joint position and setup joint motor data from the plurality of setup joints and corresponding first plurality of motors.

8. The preventive maintenance method according to claim 6, wherein the individual of the plurality of robotic arms further includes a second plurality of motors for moving corresponding of the plurality of active joints of the robotic arm, and the first plurality of printed circuit assemblies includes a second printed circuit assembly for gathering active joint position and active joint motor data from the plurality of active joints and corresponding second plurality of motors.

9. The preventive maintenance method according to claim 1, wherein the components include a battery.

10. The preventive maintenance method according to claim 1, wherein the usage-related information includes a time that power is on for one of the components.

11. The preventive maintenance method according to claim 1, wherein the usage-related information includes a cycle count of a number of times that one of the components is powered up and down.

12. The preventive maintenance method according to claim 1, wherein the usage-related information includes a measure of time since installation of one of the components.

13. The preventive maintenance method according to claim 12, wherein a calendar date of the installation is stored in the non-volatile memory respectively associated with the component.

14. The preventive maintenance method according to claim 12, wherein a calendar date of the installation is stored along with a serial number of the component in a system configuration file of the medical robotic system.

15. The preventive maintenance method according to claim 1, wherein the usage-related information includes a measure of time since a last preventive maintenance was performed for one of the components.

16. The preventive maintenance method according to claim 15, wherein a calendar date of the last preventive maintenance for the component is stored in the non-volatile memory respectively associated with the component.

17. The preventive maintenance method according to claim 15, wherein a calendar date of the last preventive maintenance for the component is stored in a system configuration file of the medical robotic system.

18. The preventive maintenance method according to claim 1, wherein the usage-related information includes a count of a number of medical procedures performed using one of the components.

19. The preventive maintenance method according to claim 1, wherein the usage-related information includes an accumulated period of time that one of the components is electrically conducting.

20. The preventive maintenance method according to claim 1, wherein the components include a patient-side unit having a spring that is extendable along a vertical direction to assist in setting up a corresponding robotic arm of the patient-side unit, and the usage-related information includes a count of a number of times the spring changes direction in each of a plurality of zones defined along the vertical direction.

21. The preventive maintenance method according to claim 1, wherein the determination of whether one or more usage thresholds for the components are exceeded is performed during a power up process performed by the medical robotic system.

22. The preventive maintenance method according to claim 1, wherein the messages are displayed during a power up process performed by the medical robotic system.

23. A preventive maintenance method for a medical robotic system, comprising:
   storing usage-related information for components of the medical robotic system in non-volatile memories respectively associated with the components, wherein the components include subsystems, and wherein the storing of usage-related information comprises: determining whether a usage-related countable event has occurred for one of the subsystems, incrementing a count in a field dedicated to the usage-related countable event in one of the non-volatile memories respectively associated with the components, and adding an entry in an event list in conjunction with incrementing of the count, wherein the entry includes a date of the incrementing and an identification of the usage-related countable event causing the incrementing;
   determining whether one or more usage thresholds for the components are exceeded according to the stored usage-related information; and
   displaying messages on a display screen of the medical robotic system identifying individual of the components to be recommended for preventive maintenance based upon such determination of whether one or more usage thresholds for the components are exceeded.

24. The preventive maintenance method according to claim 23, wherein the non-volatile memory respectively associated with the subsystem is an electrically programmable read only memory.

25. The preventive maintenance method according to claim 23, wherein the non-volatile memory respectively associated with the subsystem is a flash electrically erasable and programmable read only memory, and the incrementing of the count is performed so as not to require erasure of any previously programmed bits in the flash electrically erasable and programmable read only memory.

26. A preventive maintenance method for a medical robotic system, comprising:
   storing usage-related information for components of the medical robotic system in non-volatile memories respectively associated with the components, wherein the components include subsystems, and wherein the components include joint related components of the medical robotic system;
   determining whether one or more usage thresholds for the components are exceeded according to the stored usage-related information; and
   displaying messages on a display screen of the medical robotic system identifying individual of the components to be recommended for preventive maintenance based upon such determination of whether one or more usage thresholds for the components are exceeded.

27. A preventive maintenance method for a medical robotic system, comprising:
   storing usage-related information for components of the medical robotic system in non-volatile memories respectively associated with the components, wherein the components include a patient-side unit having a spring that is extendable along a vertical direction to assist in setting up a corresponding robotic arm of the patient-side unit, and wherein the usage-related information includes a count of a number of direction changes of the spring in the vertical direction;
   determining whether one or more usage thresholds for the components are exceeded according to the stored usage-related information; and
   displaying messages on a display screen of the medical robotic system identifying individual of the components to be recommended for preventive maintenance based upon such determination of whether one or more usage thresholds for the components are exceeded.

28. A preventive maintenance method for a medical robotic system, comprising:
   storing usage-related information for components of the medical robotic system in non-volatile memories respectively associated with the components, wherein the components include subsystems;
   determining whether one or more usage thresholds for the components are exceeded according to the stored usage-related information;
   displaying messages on a display screen of the medical robotic system identifying individual of the components to be recommended for preventive maintenance based upon such determination of whether one or more usage thresholds for the components are exceeded; and
   updating a system configuration file of the medical robotic system with the usage-related information stored in the non-volatile memories, wherein the updating of the system configuration file is performed during a power down process of the medical robotic system.

29. The preventive maintenance method according to claim 28, wherein the determination of whether one or more usage thresholds for the components are exceeded, comprises:
   reading an item from the system configuration file; and
   determining whether the item has exceeded one or more usage thresholds for one of the components related to the item.

30. A preventive maintenance method for a medical robotic system, comprising:
   storing usage-related information for components of the medical robotic system in non-volatile memories respectively associated with the components;
   determining whether one or more usage thresholds for the components are exceeded according to the stored usage-related information;
   displaying messages on a display screen of the medical robotic system identifying individual of the components to be recommended for preventive maintenance based upon such determination of whether one or more usage thresholds for the components are exceeded; and copying a snapshot of the contents of the non-volatile memories to a removable memory unit during a power down process performed by the medical robotic system.

31. The preventive maintenance method according to claim 30, wherein the removable memory unit is insertable into a memory slot in a surgeon console of the medical robotic system.

32. A preventive maintenance method for a medical robotic system, comprising:
   storing usage-related information for components of the medical robotic system in non-volatile memories respectively associated with the components;
   determining whether one or more usage thresholds for the components are exceeded according to the stored usage-related information;
   displaying messages on a display screen of the medical robotic system identifying individual of the components to be recommended for preventive maintenance based upon such determination of whether one or more usage thresholds for the components are exceeded; and
   communicating the stored usage-related information to a remote location over a communication medium.

33. The preventive maintenance method according to claim 32, wherein the communication medium is the Internet.

34. The preventive maintenance method according to claim 32, wherein the communication medium is a telephone line.

35. A preventive maintenance method for a medical robotic system, comprising:
   storing usage-related information for components of the medical robotic system in non-volatile memories respectively associated with the components;
   determining whether one or more usage thresholds for the components are exceeded according to the stored usage-related information;
   displaying messages on a display screen of the medical robotic system identifying individual of the components to be recommended for preventive maintenance based upon such determination of whether one or more usage thresholds for the components are exceeded, wherein the displaying of messages on the display screen of the medical robotic system comprises: displaying an error message if a first usage threshold is exceeded and displaying a warning message if a second usage threshold that is lower than the first usage threshold is exceeded; and
   transitioning the medical robotic system into an error state so that a medical procedure may not be performed using the medical robotic system if the error message is to be displayed as a result of the first usage threshold being exceeded.

* * * * *